US00PP10977P

United States Patent [19]

Fick

[11] Patent Number: Plant 10,977

[45] Date of Patent: Jun. 22, 1999

[54] NEMESIA PLANT NAMED 'TIKTOC'

[75] Inventor: Amanda Fick, New Plant Nursery, South Africa

[73] Assignee: Outeniqua Nursery, Emerald, Australia

[21] Appl. No.: 08/977,482

[22] Filed: Nov. 24, 1997

[51] Int. Cl.[6] ..... A01H 5/00

[52] U.S. Cl. ..... Plt./263

[58] Field of Search ..... Plt./68.1, 263

[56] References Cited

PUBLICATIONS

Huxley et al. (Eds.) "Nemesia", The New R.H.S. Dictionary of Gardening, The Stockton Press New York. vol. 3 pp. 299, 1992.

Docherty. Self—incompatability in Nemesia. Heredity vol. 48, No. 1, pp. 137–138, 1982.

*Primary Examiner*—Howard J. Locker
*Assistant Examiner*—Melissa L. Kimball
*Attorney, Agent, or Firm*—C. A. Whealy

[57] ABSTRACT

A distinct cultivar of Nemesia plant named 'Tiktoc', characterized by its upright, rounded and compact growth habit; moderate vigor; and numerous white flowers.

1 Drawing Sheet

The present invention relates to a new and distinct cultivar of Nemesia plant, botanically known as *Nemesia foetens*, and hereinafter referred to by the cultivar name Tiktoc. The new Nemesia is marketed under the name 'Compact Innocence'.

The new cultivar is a product of a planned breeding program conducted by the inventor in George East, South Africa. The objective of the breeding program was to create new Nemesia cultivars with compact growth habit and superior flowering characteristics.

The cultivar Tiktoc originated from a cross made by the inventor of a nonpatented selection of *Nemesia foetens* as the male or pollen parent with the inventor's proprietary *Nemesia foetens* selection number 54 as the female or seed parent.

Asexual reproduction of the new Nemesia by terminal cuttings taken at George East, South Africa, has shown that the unique features of this new Nemesia are stable and reproduced true to type in successive generations.

The cultivar Tiktoc as not been observed under all possible environmental conditions. The phenotype may vary somewhat with variations in environment such as temperature, light intensity, and fertility level, without, however, any variance in genotype.

Compared to plants of the *Nemesia foetens* cultivar Innocence (not patented), plants of the new cultivar are more uniform and rounded, shorter, more freely branching, have smaller leaves and have more flowers.

The following traits have been repeatedly observed and are determined to be the unique characteristics of 'Tiktoc'. These characteristics in combination distinguish 'Tiktoc' as a new and distinct cultivar:

1. Upright, rounded and compact growth habit.
2. Moderate vigor.
3. Numerous white flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. The photograph at the top of the sheet comprises a top perspective view of a typical container plant of the cultivar Tiktoc. The photograph at the bottom of the sheet comprises a close-up view of typical flowers of 'Tiktoc'. Flower and foliage colors in the photograph may appear different than the actual colors due to light reflectance.

DETAILED BOTANICAL DESCRIPTION

The following observations and measurements describe plants grown during the spring and summer in Encinitas, Calif. under full sun with day and night temperatures averaging 24° and 16° C., respectively. Color references are made to The Royal Horticultural Society Colour Chart except where general terms of ordinary dictionary significance are used.

Botanical classsification: *Nemesia foetens* cultivar Tiktoc.

Parentage:

- *Male, or pollen, parent.*—*Nemesia foetens* selection (not patented).
- *Female, or seed, parent.*—*Nemesia foetens* proprietary selection number 54 (not patented).

Propagation:

- *Type.*—by cuttings.
- *Time to initiate roots.*—About 16 days at temperatures of 21° C.
- *Time to develop roots.*—About 28 days at temperatures of 21° C.
- *Rooting habit*—Numerous and fine.

Plant description:

- *Form.*—Compact, rounded and upright herbaceous annual.
- *Branching habit.*—Freely branching, multiple branches with secondary laterals.
- *Plant height.*—About 27 cm.
- *Plant diameter.*—About 40 cm.
- *Vigor.*—Moderate.
- *Lateral stem description.*—Square-stemmed. Internode length: About 4.4 mm. Diameter: About 2.5 mm. Texture: Glabrous. Color: 144B.
- *Foliage description.*—Leaves single, opposite and generally symmetrical. Usually about 9 leaves per lateral branch. Length: About 2.5 cm. Width: About 1 cm. Shape: Lanceolate. Apex: Acute. Base: Acute. Margin: Slightly serrate. Texture: Smooth. Color: Young leaves, upper surface: 137A. Young leaves, lower surface: 137B. Mature leaves, upper surface: 137A. Mature leaves, lower surface: 137C. Venation, upper surface: 137A. Venation, lower surface: 137C. Petiole: Length: About 4 mm. Diameter: About 1 mm. Color: 137D.

FLOWER DESCRIPTION:

*Flower type and habit.*—Flowers solitary and terminal, usually 16 to 18 flowers per terminal cluster. Flowers zygomorphic with four petals fused at their base and basal fifth bi-labiate petal modified with nectar spur. Very floriferous. Flowers self-cleaning.

*Natural flowering season.*—Spring through fall.

*Fragrance.*—None.

*Flower size.*—Length: About 1.5 cm. Diameter: About 1.3 cm.

*Petals.*—Appearance: Smooth. Length: Upper four fused petals, entire unit: About 1.2 cm. Lower fifth petal: About 7 mm. Width: Upper four fused petals, entire unit: About 1 cm. Lower fifth petal: About 5 mm. Shape: Upper four fused petals, entire unit: Rounded. Lower fifth petal: Bilobate. Margin: Entire. Color: When opening, upper surface: 155D. When opening, lower surface: 155D. Fully opened, upper surface: 155D, nectar guide on lower fifth petal, 13A. Fully opened, lower surface: 155D.

*Peduncle.*—Angle: Acute. Strength: Slender and flexible, but strong enough to support flowers. Length: About 1.5 cm. Color: 144A.

*Flower bud.*—Length: About 6 mm. Diameter: About 4 mm. Color: 155A.

*Calyx.*—Shape: Five-parted star fused at base. Length: About 5 mm. Diameter: About 2.5 mm. Sepal Shape: Linear, acute. Sepal apex: Acute. Sepal margin: Entire. Sepal texture: Smooth. Color, both surfaces: 143B.

*Reproductive organs.*—Androecium: Stamen number: Four. Stamen shape: Ovate. Anther size: Less than 0.5 mm. Anther color: 6A. Amount of pollen: Low. Pollen color: 6A. Gynoecium: Pistil length: About 5 mm. Stigma shape: Flat. Style length: About 5 mm. Style color: 144C. Stigma color: 144C. Ovary color: 144C.

Disease resistance: The new Nemesia has not been observed to be more resistant to pathogens common to Nemesias.

Seed production: Seed production has not been observed.

It is claimed:

1. A new and distinct cultivar of Nemesia plant named 'Tiktoc', as illustrated and described.

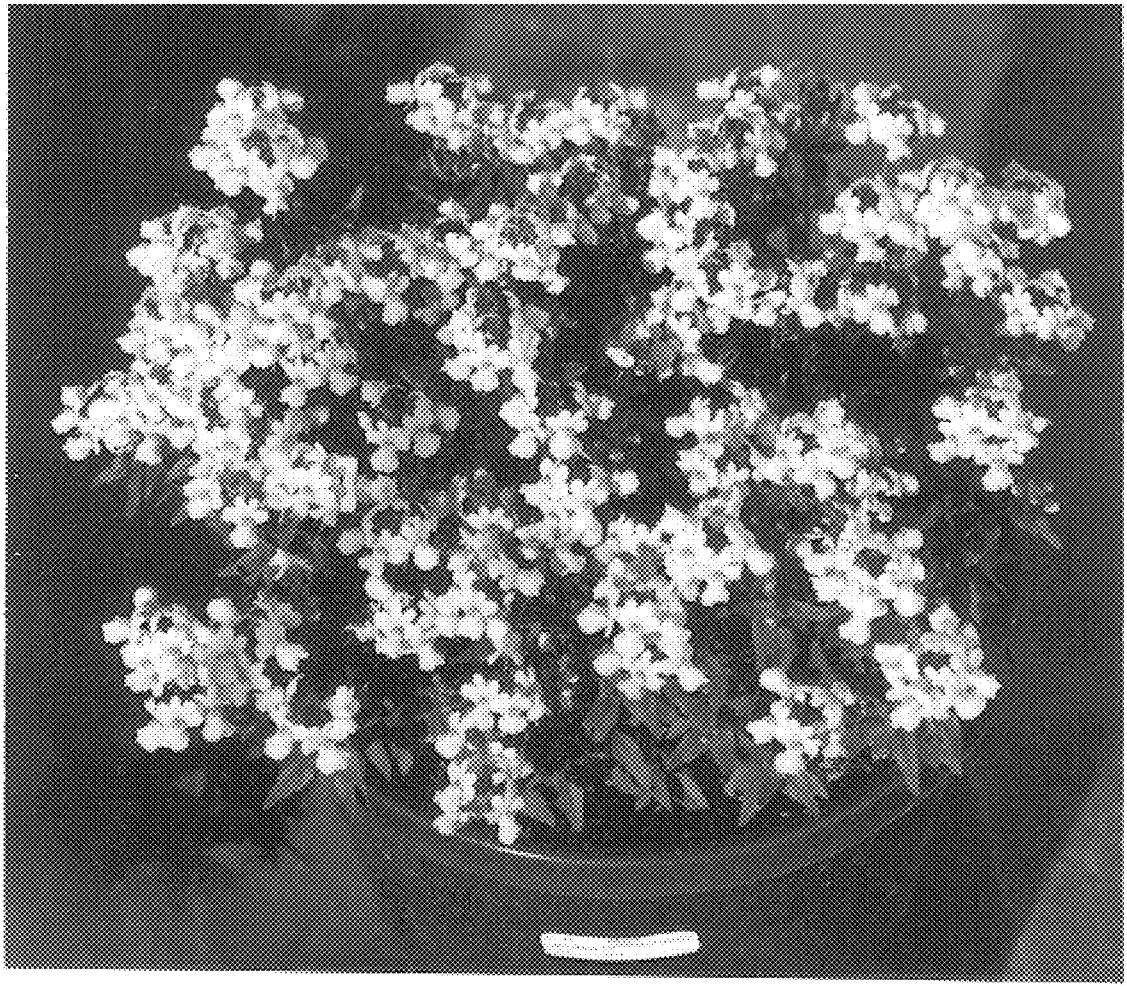
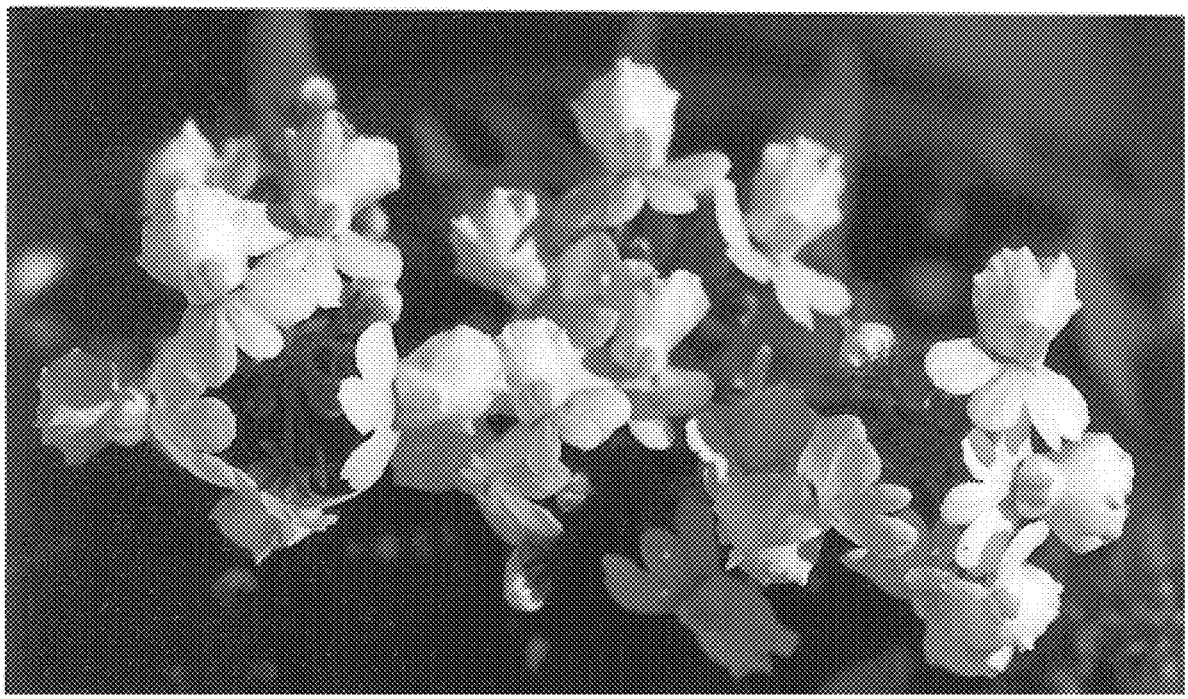

* * * * *